United States Patent
Golz et al.

[11] Patent Number: 5,384,095
[45] Date of Patent: Jan. 24, 1995

[54] APPARATUS FOR THE TRANSFER OF A DEFINED SPECIMEN QUANTITY FROM AN OUTER SPACE INTO A TEST CHAMBER

[75] Inventors: Horst Golz, Wedel; Joachim Griefan; Jörg P. Maurer, both of Hamburg, all of Germany

[73] Assignee: ANDOS Technik für die Medizin GmbH, Hamburg, Germany

[21] Appl. No.: 11,848

[22] Filed: Jan. 28, 1993

Related U.S. Application Data

[63] Continuation-in-part of Ser. No. 742,310, Aug. 8, 1991, abandoned.

[30] Foreign Application Priority Data

Aug. 8, 1990 [DE] Germany ............... 9011527
Aug. 23, 1990 [DE] Germany ............... 9012113

[51] Int. Cl.⁶ ............................................. B01L 3/02
[52] U.S. Cl. .................................. 422/100; 422/99; 422/63; 436/174; 436/180; 73/863.71; 73/863.73; 73/863.81; 73/863.85
[58] Field of Search .............. 422/99, 100, 63; 222/362; 73/863.71, 863.73, 863.81, 863.85, 863.86; 436/174, 180

[56] References Cited

U.S. PATENT DOCUMENTS

| | | | |
|---|---|---|---|
| 3,100,984 | 8/1963 | Martin | 73/863.73 |
| 3,939,409 | 2/1976 | Hogg | 73/863.73 |
| 4,702,114 | 10/1987 | Cabannes | 73/863.85 |
| 4,760,805 | 8/1988 | Smith | 111/7.2 |
| 4,823,622 | 4/1989 | Nohl et al. | 73/863.71 |
| 4,932,272 | 6/1990 | Hogg | 73/864.83 |
| 4,957,706 | 9/1990 | Romette et al. | 422/100 |
| 5,012,620 | 5/1991 | McNeil | 51/313 |

FOREIGN PATENT DOCUMENTS 3507032 8/1986 Germany .

*Primary Examiner*—James C. Housel
*Assistant Examiner*—Long V. Le
*Attorney, Agent, or Firm*—Robert W. Becker & Associates

[57] ABSTRACT

An apparatus for the transfer of a very small defined quantity of a specimen from an outer space to a reagent contained in a test chamber via a transfer slide mechanism that is displaceably disposed in a housing bore embodied as a sealing seat and that is provided with a channel that establishes the specimen quantity and is embodied as a capillary tube. The channel is adapted to be moved out of the filling position, where it is disposed in front of a receiving opening that communicates with the outer space in order to fill the channel with the specimen quantity, and into a test position in such a way that at the same time the receiving open is closed by the slide mechanism and the specimen quantity is introduced into the test chamber in order to empty the channel. The housing bore has an opening for communicating with the test chamber and is provided at this opening with a sealing lip that engages the slide mechanism in a sealing and wiping manner only when the slide mechanism is moved out of the filling position thereof and into the test position.

9 Claims, 6 Drawing Sheets

APPARATUS FOR THE TRANSFER OF A DEFINED SPECIMEN QUANTITY FROM AN OUTER SPACE INTO A TEST CHAMBER

This application is a continuation-in-part of application Ser. No. 742,310 filed Aug. 8, 1991, now abandoned.

BACKGROUND OF THE INVENTION

The present invention relates to an apparatus for the transfer of a very small defined quantity of a sample or specimen from an outer space to a reagent contained in a measuring or test chamber via a transfer slide mechanism that is displaceably disposed in a housing bore embodied as a valve or sealing seat and that is provided with passage or channel means that forms or establishes the specimen quantity and is embodied as a capillary tube, whereby the channel means is adapted to be moved out of a filling position, where it is disposed in front of a receiving opening that communicates with the outer space in order to fill the channel means with the specimen quantity, and into a measuring or test position in such a way that at the same time the receiving opening is closed by the transfer slide mechanism and the specimen quantity is introduced into the test chamber in order to empty the channel means.

DE-OS 3 507 032 discloses a transfer apparatus of this general type that is embodied as a disposable device and is essentially made of plastic; with this known device, a very small defined quantity of a specimen can be introduced into a hermetically sealed test chamber that contains a reagent without thereby having to negate the sealed aspect of the test chamber. Unfortunately, with this known apparatus, due to adhesion and/or capillary forces, some of the specimen can penetrate the sealing seat between the transfer slide mechanism and the housing bore during filling of the channel means in the slide mechanism that forms or establishes the specimen quantity. These microdrops of specimen that adhere to the transfer slide mechanism thus, in addition to the defined quantity of specimen, also enter the test chamber and therefore alter the specimen size that is to be delivered to the test chamber; this, for example by quantitative analysis, leads to significant incorrect or erroneous measurements.

It is therefore an object of the present invention to provide an apparatus for the transfer of a very small defined quantity of a specimen from an outer space into a test chamber where manufacturing tolerances and in particular physical parameters such as adhesion and capillary forces do not alter the magnitude of the defined specimen quantity that is to be delivered to the test chamber.

BRIEF DESCRIPTION OF THE DRAWINGS

This object, and other objects and advantages of the present invention, will appear more clearly from the following specification in conjunction with the accompanying schematic drawings, in which.

SUMMARY OF THE INVENTION

The transfer apparatus of the present invention is characterized primarily in that a sealing lip is formed on the housing bore, which is directed into the test chamber, with this sealing lip coming into sealing and wiping engagement with the transfer slide mechanism when the latter is shifted from the filling position into the measuring or test position.

The inventive sealing lip is provided on the housing bore where the latter opens out into the test chamber, with this sealing lip engaging the transfer slide mechanism in a sealing manner only when the transfer mechanism is moved out of its sealing position and into the test position; with such a sealing lip, even the slightest amount of specimen that adheres to the transfer slide mechanism is wiped off, so that only the defined quantity of specimen passes into the test chamber. In this connection, it is particularly advantageous for the sealing lip to have no sealing function during filling of the inventive transfer apparatus; rather, this sealing lip serves only to wipe off the microdrops of specimen that have adhered to the transfer slide mechanism. Thus, prior to use of the transfer apparatus, the sealing lip does not rest against the transfer slide mechanism, and is therefore also not subjected to any mechanical stresses that would effect a cold flow of the plastic sealing lip and could adversely affect the ability of the sealing lip to carry out its wiping function.

Pursuant to one expedient specific embodiment of the present invention, it has proven to be advantageous to provide on the transfer slide mechanism, between the channel means that establishes the specimen quantity and that end of the slide mechanism that faces the test chamber, a sealing bead that cooperates, i.e. is in contact with the housing bore in order to prevent not only a loss of reagent out of the test chamber during storage of the transfer apparatus after manufacture thereof, but also a penetration of specimen into the test chamber during filling of the specimen quantity due to a lack of sealing of the sealing seat between the housing bore and the transfer slide mechanism. It has further proven advantageous to embody the sealing bead as a resilient sealing ring that is disposed in an annular groove that is formed in the transfer slide mechanism. It should be noted that the channel means that establishes the specimen quantity can be embodied as a bore that extends through the transfer slide mechanism, or has a groove that extends over at least 180° of the outside of the transfer slide mechanism.

Further specific features of the present invention will be described in detail subsequently.

DESCRIPTION OF PREFERRED EMBODIMENTS

Figure 1:
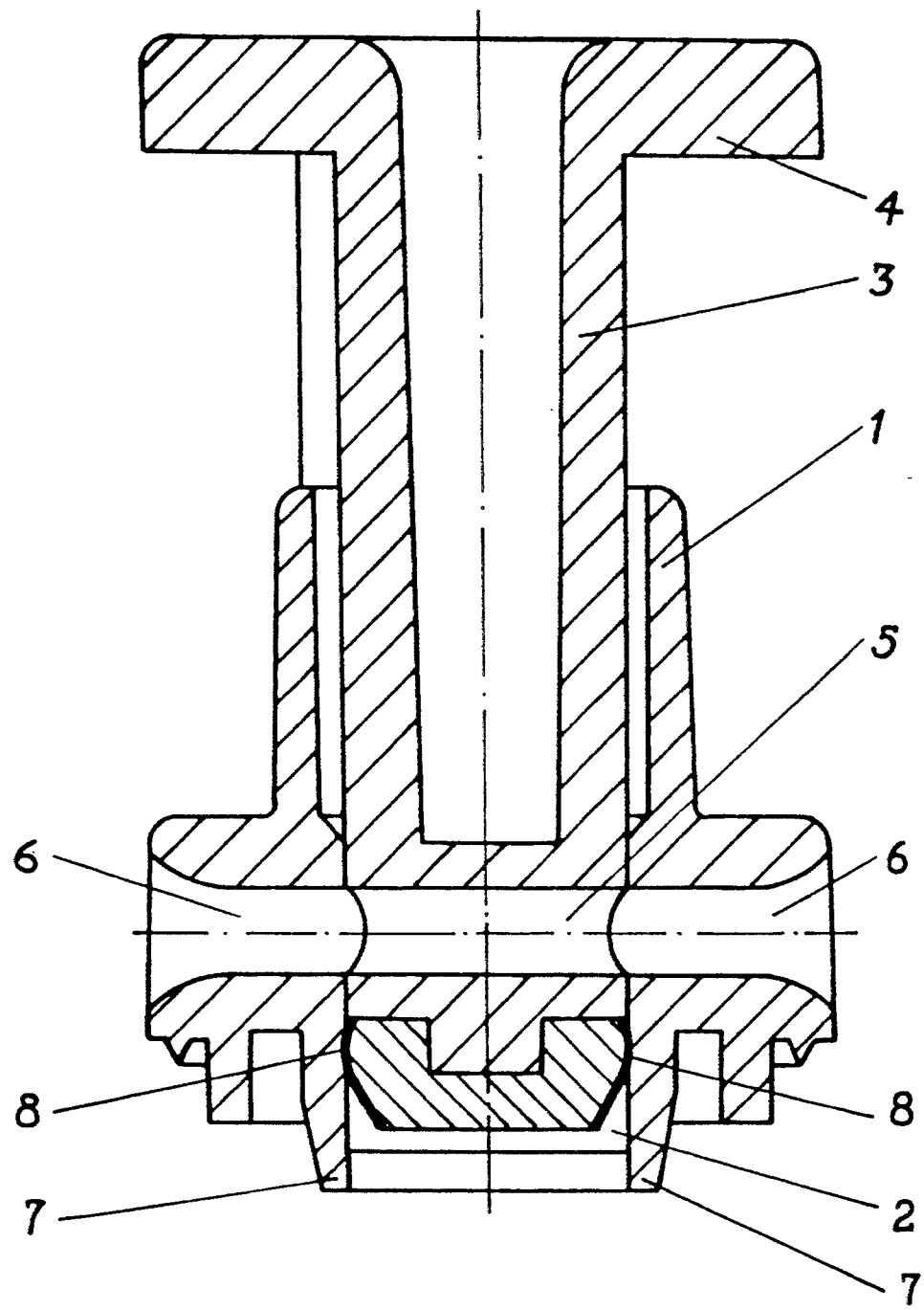
FIG. 1 is an enlarged cross-sectional view through one exemplary embodiment of the inventive transfer apparatus in the filling position.
Figure 2:
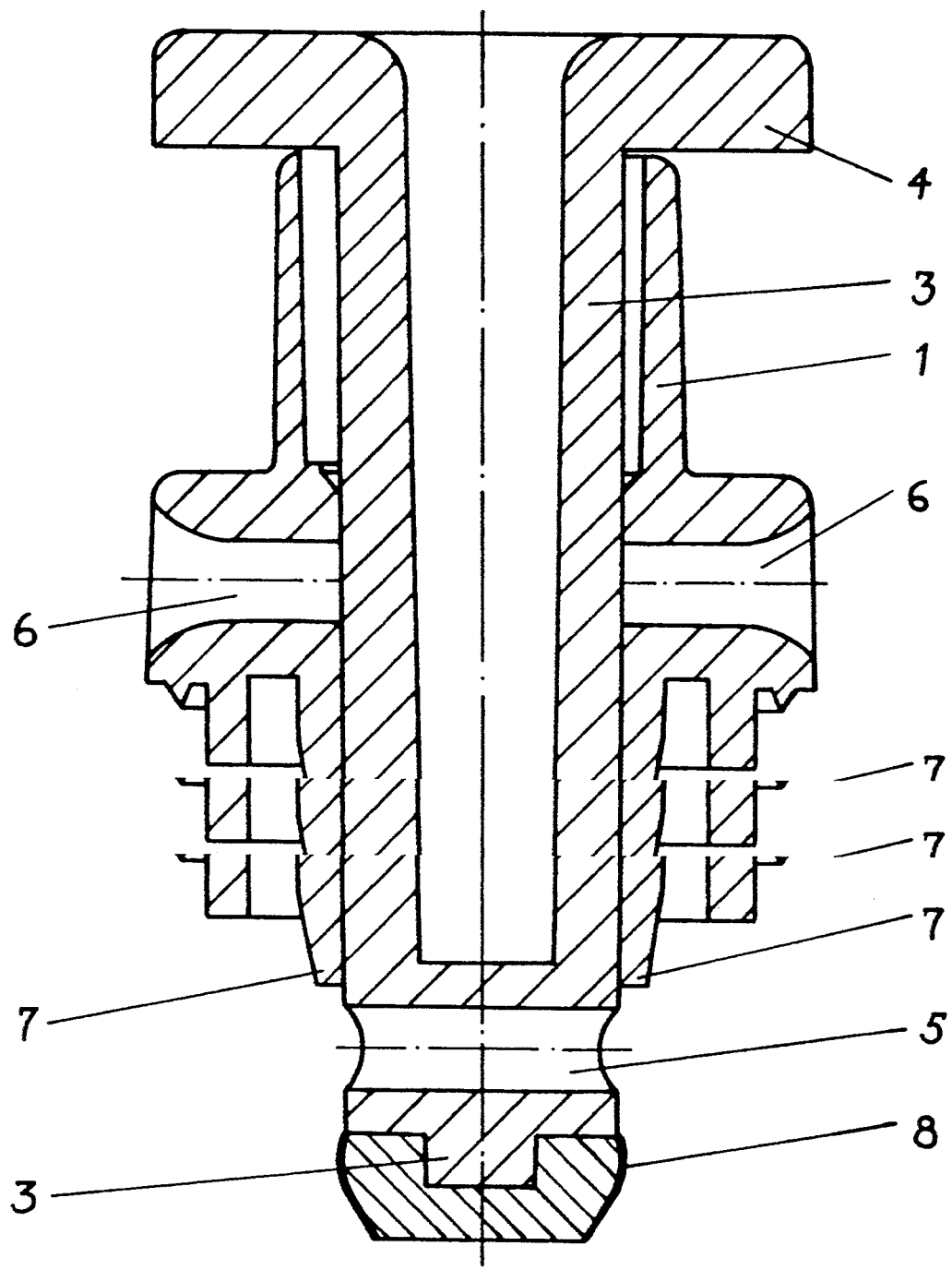
FIG. 2 is a cross-sectional view of the transfer apparatus of FIG. 1 in the measuring or test position.
Figure 3:
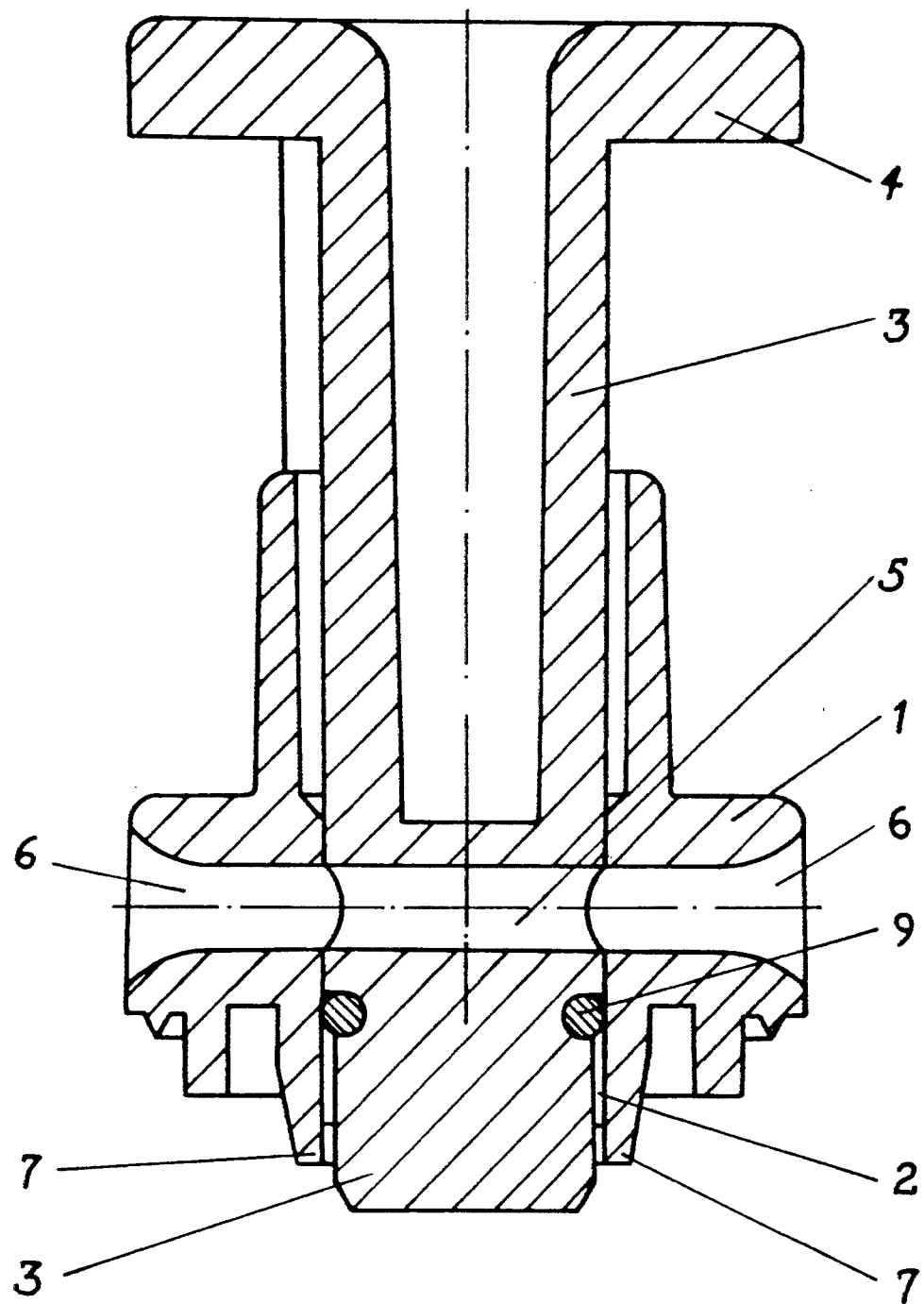
FIG. 3 is an enlarged cross-sectional view through a further exemplary embodiment of an inventive transfer apparatus in the filling position.
Figure 4:
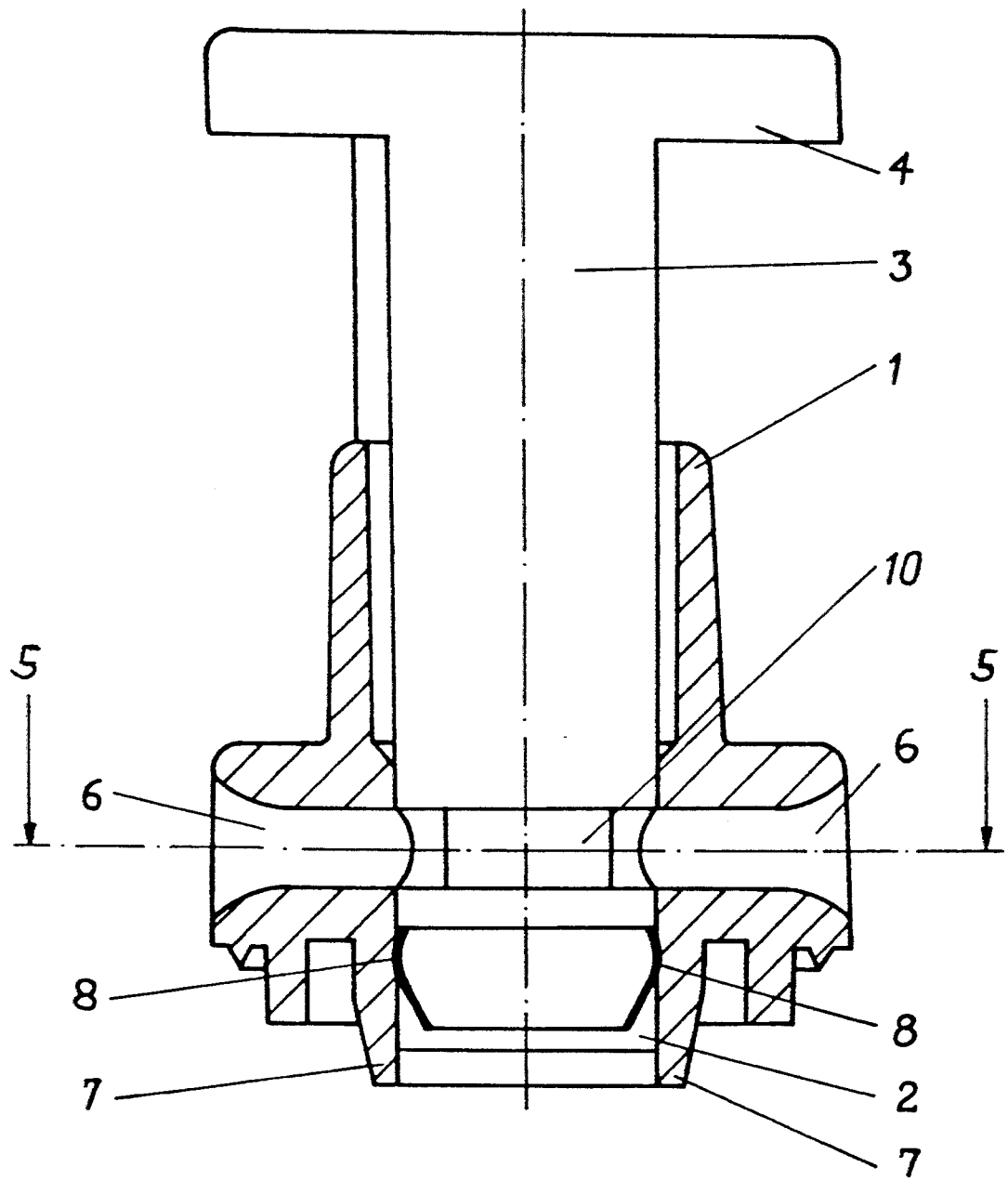
FIG. 4 is an enlarged partially cross-sectioned view through yet another exemplary embodiment of the inventive transfer apparatus in the filling position.
Figure 5:
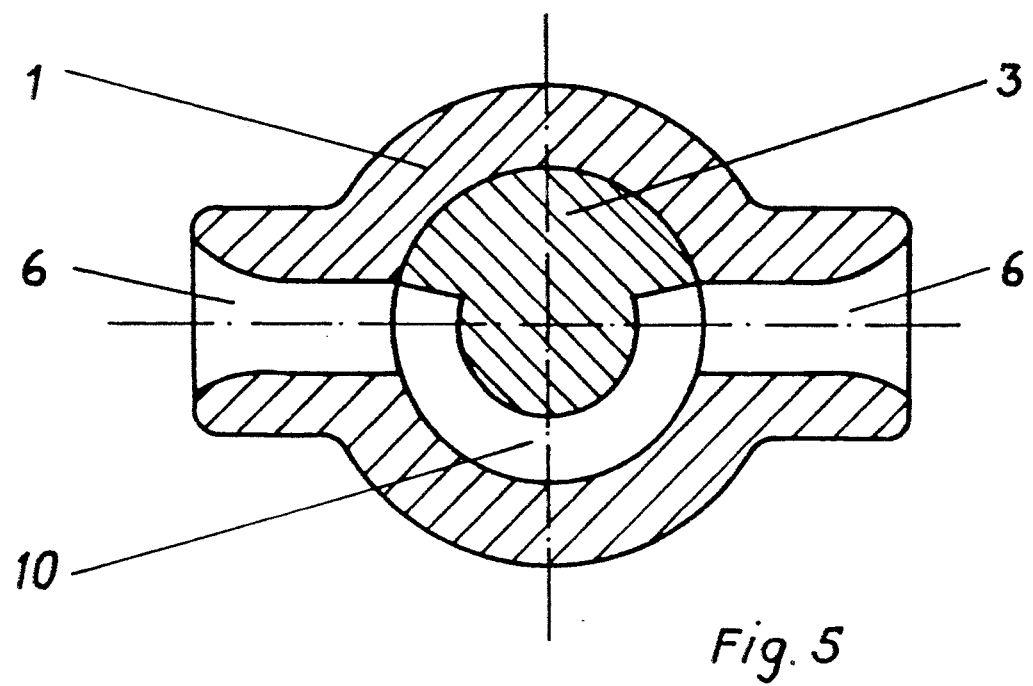
FIG. 5 is a cross-sectional view taken along the line 5—5 of the transfer apparatus of FIG. 4.

Referring now to the drawings in detail, the disposable apparatus illustrated in FIGS. 1 to 3 for transferring a defined specimen quantity from an outer space to a reagent contained in a test chamber comprises a plastic housing 1 having an axial bore 2 in which is disposed a plunger-like transfer slide mechanism 3. The surfaces of the housing bore 2 and the slide mechanism 3 that contact one another form a valve or sealing seat. The transfer slide mechanism 3 is provided at one end with a push plate 4. In the embodiments illustrated in FIGS. 1-3, 5 and 6 a bore 5 in the form of a capillary tube passes through the slide mechanism 3, whereas in the embodiment illustrated in FIGS. 4 and 5, the slide mechanism 3 is provided with a groove 10 that is similarly embodied as a capillary tube and on the outside extends over at least 180°; the bore 5 and groove 10 establish the specimen quantity. In the filling position of the transfer slide mechanism 3 (FIGS. 1, 3 and 4, 5 and 6), the bore 5 or the groove 10 is aligned with receiving openings 6 provided in the housing 1. An annular sealing lip 7 is formed-on at that end of the housing that is opposite the push plate 4 of the transfer slide mechanism 3 and where an opening of the housing bore 2 to the non-illustrated test chamber is provided. The inside diameter of the sealing lip 7 is less than that of the housing bore 2, i.e. is less than the outer diameter of the transfer slide mechanism 3 in the vicinity of the bore 5 or groove 10 thereof.

In the embodiments of the transfer apparatus illustrated in FIGS. 1, 2, 4 and 6, the transfer slide mechanism 3, in the end region opposite the push plate 4, has a sealing bead 8 that in the filling position of these apparatus (FIGS. 1, 4 and 6) rests in a sealing manner against the wall of the housing bore 2. In addition, as will be described in greater detail subsequently, in the embodiment illustrated in FIG. 6, the sealing lip 7 also rests against the transverse slide mechanism 3, i.e. the sealing bead 8 of the lower portion thereof, already in the filling position.

In the embodiment of the inventive transfer apparatus illustrated in FIG. 3, this sealing bead is embodied as a resilient sealing ring 9 that is disposed in an annular groove formed in the transfer slide mechanism 3.

The inventive transfer apparatus is manufactured with a fixedly attached, yet not illustrated, measuring or test chamber that contains a predetermined amount of reagent, and is delivered with the transfer slide mechanism 3 in the filling position, in which the sealing bead 8 or sealing ring 9 rests against the housing bore 2 between where the latter opens into the test chamber and the receiving openings 6, so that especially while the transfer apparatus is being stored, the sealing head 8 prevents reagent from escaping from the test chamber via the sealing seat between the housing bore 2 and the transfer slide mechanism 3. In addition, during filling of the specimen space 5 or 10, the sealing bead 8 or sealing ring 9 prevents any of the specimen from accidentally passing prematurely in the opposite direction into the test chamber. The function of the sealing bead 8 can be clearly understood from the enlarged and exaggerated showing of the drawings, which schematically illustrate that the plastic body of the housing 1, and in particular the bore 2 thereof, is slightly elastically enlarged or expanded by the sealing bead 8, while the slide mechanism 3, in the vicinity of this sealing bead 8, is slightly compressed. The drawings attempt to schematically illustrate this situation.

After the bore 5 or groove 10 has been filled with specimen, pressure is exerted upon the pressure or push plate 4 of the transfer slide mechanism 3 to displace the same out of the filling position shown in FIG. 1 and into the measuring or test position shown in FIG. 2. In so doing, the transfer slide mechanism 3 comes into engagement with the sealing lip 7, which wipes off any of the specimen that is adhering to the transfer slide mechanism 3, so that only that quantity of specimen that is present in the bore 5 or groove 10 is fed or introduced into the test chamber, where it reacts with the reagent, thereby precluding test errors.

Figure 6:
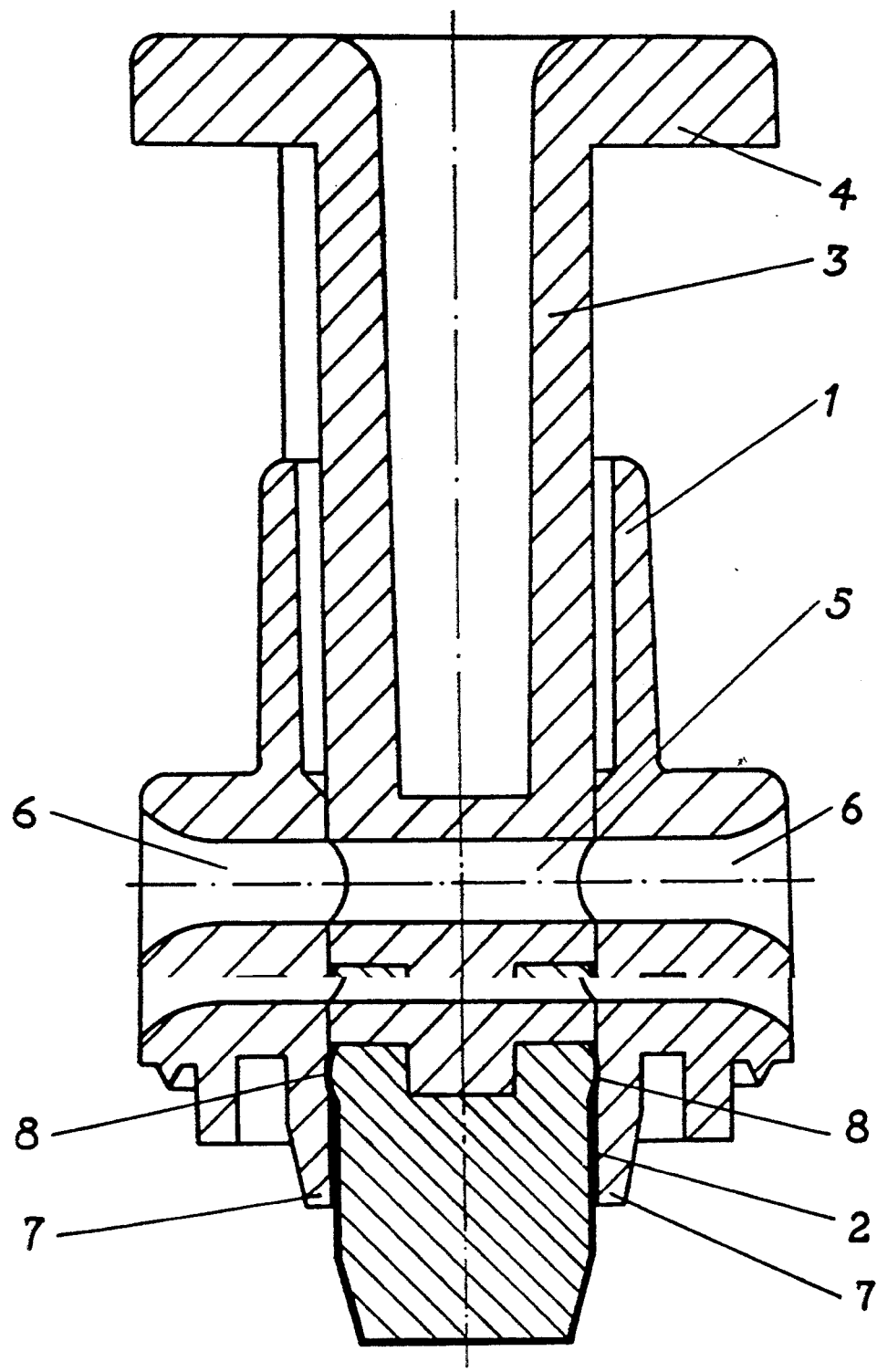
FIG. 6 is an enlarged cross-sectional view of another exemplary embodiment of the inventive transfer apparatus in the filling position.

In the further preferred embodiment of FIG. 6, the transfer slide mechanism 3 is again provided with a lower portion that is provided with the sealing bead 8. However, in this embodiment, in contrast to the embodiments of FIGS. 1, 2 and 4, 5, the lower portion of the transfer slide mechanism 3 extends beyond the sealing lip 7. Thus, with this embodiment the sealing lip 7 already rests against the transfer slide mechanism 3, i.e. the lower portion thereof, in the filling position. The advantage offered by the embodiment of FIG. 6 is that in addition to the sealing bead 8, a further sealing means is provided to prevent reagent from escaping from the test chamber during storage of the inventive transfer apparatus. Again, the inside diameter of the sealing lip 7 is less than the outer diameter of the transfer slide mechanism 3 in the vicinity of the bore 5 thereof.

As described previously, the transfer slide mechanism 3, in the end region opposite the push plate 4, can be provided with a sealing bead 8. This sealing bead can, for example, be integrally formed on the transfer slide mechanism 3, can be glued thereon, or can otherwise be produced with the transfer slide mechanism 3 via an appropriate two-component process, such as a two-component extrusion process.

The entire transfer apparatus of the present invention is made of plastic. By way of example only, the upper part of the transfer slide mechanism 3 that is provided with the bore 5 or groove 10 can be made of polypropylene, whereas the lower portion of the transfer slide mechanism that is provided with the sealing bead 8 can be of acrylonitrile-butadiene-styrene (ABS) copolymers; the housing 1 can also be made of polypropylene. However, it is to be understood that the components of the inventive transfer apparatus could also be made of other plastics that do not chemically react with the reagent or with the specimen, and that have physical properties, especially with regard to elasticity and strength, that ensure the inventively provided seal between the transfer slide mechanism 3 and the housing bore 2, i.e. the sealing lip 7.

As has been previously indicated, the inventive apparatus deals with the transfer of a very small defined quantity of a sample or specimen. Again by way of example only, the volume of such a specimen can be of the order of magnitude of approximately 10 $mm^3$, whereby the diameter of the capillary tube or bore 5 would be about 1.6 mm, and the diameter of the transfer slide mechanism 3 would be about 5 mm.

The present invention is, of course, in no way restricted to the specific disclosure of the specification and drawings, but also encompasses any modifications within the scope of the appended claims.

What we claim is:

1. In an apparatus for transferring a defined quantity of a specimen from an outer space to a reagent contained in a test chamber by a transfer slide mechanism that is displaceably disposed in a bore of a housing, said bore serving as a sealing seat, with said slide mechanism being provided with channel means that establishes the specimen quantity and is in the form of a capillary tube, whereby said transfer slide mechanism and said channel means are movable out of a filling position, where said channel means communicates with a receiving opening that in turn communicates with said outer space in order to fill said channel means with said specimen quantity, and into a test position wherein said receiving opening is closed by said transfer slide mechanism and said specimen quantity is introduced into said test chamber in order to empty said channel means, the improvement wherein:

said housing bore has an opening for communicating with said test chamber and said housing including at said housing bore opening a sealing lip that engages said transfer slide mechanism in a sealing and wiping manner when said transfer slide mechanism is moved out of said filling position thereof and into said test position, whereby in said filling position of said transfer slide mechanism, the inside diameter of said sealing lip is less than the outer diameter of said transfer slide mechanism in the vicinity of said channel means thereof and is also less than the inside diameter of said housing bore in the vicinity of said receiving opening of said housing.

2. An apparatus according to claim 1, in which said transfer slide mechanism, between said channel means and an end of said transfer slide mechanism that is directed toward said test chamber, is provided with a sealing bead that is in contact with a region of said housing bore disposed between said receiving opening and said sealing lip.

3. An apparatus according to claim 2, in which said sealing bead is in the form of a resilient sealing ring that is disposed in an annular groove formed in said transfer slide mechanism.

4. An apparatus according to claim 1, in which said channel means is a bore that extends through said transfer slide mechanism.

5. An apparatus according to claim 1, in which said channel means is a groove that extends over at least 180° of an outside surface of said transfer slide mechanism.

6. An apparatus according to claim 1, wherein said sealing lip engages said transfer slide mechanism in a sealing and wiping manner only when said transfer slide mechanism is moved out of said filling position thereof and into said test position.

7. An apparatus according to claim 2, wherein said sealing bead is disposed on a lower portion of said transfer slide mechanism that is directed toward said test chamber.

8. An apparatus according to claim 7, wherein said lower portion of said transfer slide mechanism extends beyond said sealing lip remote from said receiving opening, with said sealing lip already engaging said lower portion of said transfer slide mechanism in said filling position thereof.

9. An apparatus according to claim 7, wherein said housing and said portion of said transfer slide mechanism that is provided with said channel means are made of polypropylene, while said lower portion of said transfer slide mechanism with said sealing bead is made of an ABS copolymer.

* * * * *